(12) United States Patent
Fassi

(10) Patent No.: US 6,673,837 B2
(45) Date of Patent: Jan. 6, 2004

(54) ACETYL L-CARNITINE SALT WITH A DICARBOXYLIC ORGANIC ACID AND PROCESS FOR PREPARING SAME

(76) Inventor: Aldo Fassi, Via Nomentama 323, Rome (IT), 00162

(*) Notice: Subject to any disclaimer, the term of this patent is extended or adjusted under 35 U.S.C. 154(b) by 0 days.

(21) Appl. No.: 10/207,993

(22) Filed: Jul. 31, 2002

(65) Prior Publication Data

US 2003/0119904 A1 Jun. 26, 2003

(30) Foreign Application Priority Data

Dec. 12, 2001 (IT) ..................................... RM2001A0729

(51) Int. Cl.⁷ ....................... A61K 31/225; C07C 67/02
(52) U.S. Cl. ........................................ 514/547; 560/253
(58) Field of Search ........................... 514/547; 560/253

(56) References Cited

U.S. PATENT DOCUMENTS 4,602,039 A * 7/1986 Cavazza

* cited by examiner

*Primary Examiner*—Johann Richter
*Assistant Examiner*—Paul A. Zucker
(74) *Attorney, Agent, or Firm*—Oblon, Spivak, McClelland, Maier & Neustadt, P.C.

(57) ABSTRACT

A novel solid, crystalline and non-hygroscopic substance consisting of acetyl L-carnitine acid fumarate and a process for preparing same are disclosed.

15 Claims, No Drawings

ACETYL L-CARNITINE SALT WITH A DICARBOXYLIC ORGANIC ACID AND PROCESS FOR PREPARING SAME

BACKGROUND OF THE INVENTION

1. Field of the Invention

The present invention relates to acetyl L-carnitine acid fumarate, hereinbelow briefly ALCFH, as a novel solid, crystalline and non-hygroscopic substance, a process for preparing same and the compositions comprising said substance as active principle.

In order to precisely understand the present invention, a clear distinction should be made between the formula unit

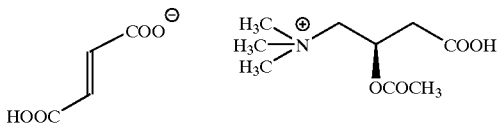

of acetyl L-carnitine acid fumarate and the ionic compound or substance composed of fumarate and 2-(acetyloxy)-3-carboxy-N,N,N-trimethyl-1-propanaminium ions. As known, different spatial arrangements of the same constituent anions and cations may give rise to ionic substances showing totally distinct sets of physico-chemical characteristics, even though these substances are represented by the same formula unit. Such substances may, therefore, differ in the properties typical of the solid-crystalline state, such as e.g. melting point, specific melting heat, crystalline system, etc. as well as in those properties particularly relevant to their industrial applicability, such as flowability (when they occur as powder or granules), non-hygroscopicity, shelf-life and the like.

By "solid crystalline substance" is meant herein the ALCFH of the present invention, i.e. the substance in the form of a crystalline solid (these terms having the current meaning they take on in the technical-scientific terminology), having melting point of 105–110° C.

By "non-hygroscopic substance" is meant herein a substance showing the ability possessed by the ALCFH of the present invention, to withstand a relative humidity of a least 60%, at 25° C., for 24 hours, when it occurs as powder or granules, without giving rise to adverse phenomena of clotting, agglomeration or even deliquescence which result in loss of their flowability.

By "hygroscopic" is meant herein the bothersome property shown by most of L-carnitine and alkanoyl L-carnitine salts (particularly by their "inner salts") to undergo, when they occur as powders or granules, significant alteration of their flowability due to their clotting, agglomeration or even deliquescence, following exposure to an environment of relative humidity lower than 50–60%, at 25° C., for 24 hours.

2. Description of the Prior Art

The problems of storage and processing brought about by the high hygroscopicity of L-carnitine and alkanoyl L-carnitine inner salts (among which acetyl L-carnitine inner salt) have long since been known. This high hygroscopicity renders the manufacture and storage of orally administrable solid presentation forms particularly troublesome.

However, administration forms such as tablets and capsules represent the preferred presentation forms in as much as they make it particularly easy for users to take the active ingredient and comply with optimal dosage regimens.

The problem of L-carnitine and alkanoyl L-carnitine inner salts hygroscopicity has been solved by converting these inner salts into salts of pharmacologically acceptable acids, based on the assumption that such salts maintain the same therapeutical/nutritional activities of the inner salts and do not exhibit unwanted toxic or side effects.

The finding of those pharmacologically acceptable acids which possess the ability to convert the aforesaid carnitines into stable and non-hygroscopic salts is carried out on a purely empirical basis, since no theoretical assumptions are known for selection thereof.

Although there is now an extensive body of literature, particularly patents, disclosing the production of allegedly stable, non-hygroscopic carnitine salts, actually only L-carnitine acid fumarate (U.S. Pat. No. 4,602,039 Sigma-Tau), L-carnitine L-(+)-tartrate (U.S. Pat. No. 5,703,376 Lonza) and, more recently, acetyl L-carnitine galactarate (U.S. Pat. No. 5,952,379 Sigma-Tau) have been developed on an industrial scale and marketed to date.

U.S. Pat. No. 4,602,039 (which is incorporated herein by reference) discloses a class of non-hygroscopic salts of L-carnitine and acetyl, propionyl and butyryl L-carnitine wherein the anion moieties are the anions of pharmacologically acceptable acids, among which fumarate is cited.

Fumarate anion shows remarkable advantages over the anions of other pharmacologically acceptable acids insofar as it is an intermediate in the Krebs' cycle and is, therefore, a natural substance physiologically present in the human body, as L-carnitine and acetyl L-carnitine are.

Fumarate's ability in assisting the metabolism of ischaemic myocardium by enhancing ATP's production as well as its efficacy in free radicals scavenging have been demonstrated.

The aforesaid patent discloses, inter alia, L-carnitine acid fumarate and its preparation (see Example 8). As previously indicated, L-carnitine acid fumarate shows excellent shelf-life, it is non-hygroscopic and consequently has long since been on the market.

U.S. Pat. No. 4,602,039 purports also to "disclose" the preparation of acetyl L-carnitine acid fumarate (see Example 6) which would be obtained as a non-hygroscopic solid having melting point of 159–161° C.

Actually, neither repeatedly and accurately reproducing the preparation procedures disclosed in the aforesaid Example 6 nor applying to acetyl L-carnitine acid fumarate preparation the process taught in general terms in column 2, lines 18–19 of the patent, nor modifying the operational conditions and solvent selection as disclosed therein and interpreted in the light of the current skill of an average expert in organic synthesis has it ever been possible to arrive at the aforesaid compound in the form of a solid, crystalline and non-hygroscopic substance.

On the contrary, the reaction product thus obtained presents itself as a thick gluish fluid or as a layer of glassy consistency which strongly adheres to the reaction vessel walls from which it is hardly possible to remove it. The substance thus obtained does not solidify nor it is possible to determine its melting point.

In conclusion, this substance is not an industrially usable product for any purpose, particularly for anyone of the practical purposes (prolonged shelf-life in non-dehumidified environments, lasting flowability when it occurs as powder or granules, etc.) the achievement of which justifies the conversion of the various carnitine inner salts into pharmacologically acceptable salts.

SUMMARY OF THE INVENTION

It is, therefore, the object of the present invention to provide ALCFH as a solid, crystalline and non-hygroscopic substance and a process for preparing it.

Since the teachings of U.S. Pat. No. 4,602,039 do not allow such a substance to be obtained, the solid, crystalline, non-hygroscopic substance having melting point of 105–110° C. of the present invention is, clearly, a novel substance.

The process of the present invention comprises the following steps:

(a) preparing a crystallization seed consisting essentially of acetyl L-carnitine acid fumarate by
  (a.1) adding equimolar amounts of acetyl L-carnitine inner salt and fumaric acid to a lower alkanol, heating and stirring the resulting reaction mixture till complete dissolution of the reagents, thus obtaining a solution;
  (a.2) cooling the solution to room temperature and adding thereto a precipitating agent in the minimum amount needed to obtain the formation of a precipitate of acetyl L-carnitine acid fumarate;
  (a.3) filtering off and drying the precipitate to be used as crystallization seed in step (c);
(b) preparing a solution of equimolar amounts of acetyl L-carnitine inner salt and fumaric acid in a lower alkanol, heating and stirring the resulting reaction mixture till complete dissolution of the reagents and then cooling the solution to room temperature;
(c) seeding the solution of step (b) with the minimum amount of the crystallization seed of step (a) needed to obtain a precipitate;
(d) isolating the precipitate of step (c) by filtering it off, and drying it in an oven under vacuum thus obtaining a solid, crystalline, non-hygroscopic substance having melting point of 105–110° C. comprised of acetyl L-carnitine acid fumarate.

It shall be apparent that step (a) of the process (i.e. the preparation of the crystallization seed consisting essentially of acetyl L-carnitine acid fumarate) is required when no ALCFH is available at all. However, when—following completion of step (d)—large amounts of ALCFH are produced, a minute sample of this very end product may advantageously be used as crystallization seed in step (c) of the process. Consequently, step (a) may be regarded as a method of preparing a first crystallization seed to be used in a process for manufacturing considerable amounts of ALCFH. Once a first batch of ALCFH is thus produced, small portions thereof may be used as cristallization seed in any subsequent production operation.

DESCRIPTION OF THE PREFERRED EMBODIMENTS

The lower alkanol of step (a.1) and (b) is selected from the group consisting of methanol, ethanol, propanol, isopropanol, butanol, isobutanol and the aqueous solutions thereof. Absolute ethanol and 95%–96% v/v ethanol are the preferred alkanols.

The precipitating agent of step (a.2) is selected from the group consisting of L-carnitine acid fumarate, the chlorides, carbonates and sulphates of alkali metals and alkaline-earth metals, silica and alumina. L-carnitine acid fumarate is the preferred precipitating agent.

The alkali metals and alkaline-earth metals are selected from the group consisting of sodium, potassium, magnesium and calcium. The minimum amount of the precipitating agent of step (a.2) and crystallization seed of step (c) is about 0.01–0.5% by weight to the amount of acetyl L-carnitine inner salt and fumaric acid.

In step (c) in order to increase the yield of the precipitated salt, the temperature of the seeded solution can be lowered to below room temperature, preferably to about 0° C.–10° C.

The following non-limiting examples show the preparation of the substance of the invention.

EXAMPLE 1

Preparation of the Crystallization Seed with L-carnitine Acid Fumarate as Precipitating Agent To 10 mL of 95% v/v of ethanol at about 70° C., 2.28 g (0.01 moles) of acetyl L-carnitine inner salt (titre: 89.3%) and 1.16 g (0.01 moles) of fumaric acid were added under vigorous stirring. The resulting solution ("mother solution") was cooled to room temperature while constantly keeping it under stirring. To the solution, a few milligrams of L-carnitine acid fumarate as precipitating agent were added. In few minutes a white, heavy precipitate formed which was filtered off one hour later.

The product thus isolated was placed in an oven at 30° C. under vacuum overnight and then at 50° C. under vacuum for other 4 hours. 2.13 g (yield: 66.7%) of solid, crystalline ALCFH were obtained which were used as crystallization seed in the preparations of Examples 2 and 3.

Melting point: 105–110° C.

Elementary analysis:

| Calculated | C 48.90 | H 6.63 | N 4.39 |
| Found | C 48.94 | H 6.70 | N 4.40 |

$^1$H NMR (CD$_3$OD, δ, p.p.m.); 6.72 (s, 2H, CH=CH); 5.58 (m, 1H, CH—O); 3.78 (m, 1H, CHH—N); 3.68 (m, 1H, CHH—N); 3.18 (s, 9H (CH$_3$)$_3$—N); 2.71 (dd, 1H, CHH—COO); 2.59 (dd, 1H, CHH—COO); 2.09 (s, 3H, CH$_3$—CO).

EXAMPLE 2

Preparation of ALCFH

To 100 mL of absolute ethanol, 22.76 g (0.1 moles) of acetyl L-carnitine inner salt (having the above indicated titre) and 11.61 (0.1 moles) of fumaric acid were added under stirring, while, at the same time, the mixture was heated; heating and stirring were continued till complete dissolution of the reagents.

The resulting solution was cooled to room temperature.

When the solution reached room temperature, a few milligrams of ALCFH prepared as shown in Example 1 were added thereto, whilst the temperature was lowered to 5° C.

In a few minutes a precipitate started to form which was filtered off one hour later. The product thus isolated was placed in an oven at 30° C. under vacuum overnight and then at 50° C. still under vacuum for 4 hours.

21.08 g (yield: 68.3%) of white, solid, crystalline, non-hygroscopic ALCFH were obtained.

Melting point: 105–110° C.

Elementary analysis:

| Calculated. | C 48.90 | H 6.63 | N 4.39 |
| Found. | C 48.90 | H 6.74 | N 4.36 |

$^1$H NMR (CD$_3$OD, δ, p.p.m.); 6.72 (s, 2H, CH=CH); 5.58 (m, 1H, CH—O); 3.78 (m, 1H, CHH—N); 3.68 (m, 1H, CHH—N); 3.18 (s, 9H (CH$_3$)$_3$—N); 2.71 (dd, 1H, CHH—COO); 2.59 (dd, 1H, CHH—COO); 2.09 (s, 3H, CH$_3$—CO).

EXAMPLE 3

ALCFH further Preparation

To 100 mL of 95% v/v ethanol, 22.76 g (0.1 moles) of acetyl L-carnitine inner salt (having the above indicated titre) and 11.61 g (0.1 moles) of fumaric acid were added under stirring while, at the same time, the mixture was heated; heating and stirring were continued till complete dissolution of the reagents.

The resulting solution was then cooled to room temperature, stirring was discountinued and a few milligrams of ALCFH prepared as shown in Example 1 were added. The seeded solution was cooled to about 8° C.

The solution was left to stand for 24 hours. After this time period had elapsed, good-sized globular formations of a crystalline substance were obtained, which was easily removed from the reaction vessel walls and grounded to the desired particle size.

The granulate thus obtained was placed in an oven at 30° C. under vacuum overnight and then at 50° C. still under vacuum, for 4 hours. 19.5 g (yield: 60.9%) of white, solid, crystalline and non-hygroscopic ALCFH were obtained.

Melting point: 108° C.–110° C.

Elementary analysis:

| Calculated. | C 48.90 | H 6.63 | N 4.39 |
|---|---|---|---|
| Found. | C 48.88 | H 6.70 | N 4.37 |

$^1$H NMR (CD$_3$OD, δ, p.p.m.); 6.72 s, 2H, CH=CH); 5.58 (m, 1H, CH—O); 3.78 (m, 1H, CHH—N); 3.68 (m, 1H, CHH—N); 3.18 (s, 9H (CH$_3$)$_3$—N); 2.71 (dd, 1H, CHH—COO); 2.59 (dd, 1H, CHH—COO); 2.09 (s, 3H, CH$_3$—CO).

EXAMPLES 4–10

Preparation of a Crystallization Seed with other Precipitating Agents

The procedures of Example 1 which describes the preparation of a crystallization seed consisting of ALCFH using L-carnitine acid fumarate as precipitating agent (as previously indicated, L-carnitine acid fumarate is the preferred precipitating agent) were repeated by using, instead of the latter compound, the following compounds in the form of finely divided solids, e.g. as crystalline powders:

Example 4: sodium chloride;
Example 5: sodium sulphate;
Example 6: sodium carbonate;
Example 7: lithium carbonate;
Example 8: calcium carbonate;
Example 9: alumina;
Example 10: silica.

In all of the Examples 4–10, the addition of about 0.1 mg of the above-identified compounds to the "mother solution" of Example 1 brought about, with a velocity depending on the specifically selected compound, the precipitation and crystallization of ALCFH to be used as crystallization seed in procedures such as those shown in Examples 2 and 3.

It is apparent that in the preparations of Examples 2 and 3 the above-identified precipitating agents could substitute for ALCFH of Example 1 and be used directly as crystallization seeds. The indicated procedure is, however, preferable insofar as the contamination of the end product by foreign substances (even though quite negligible) is thus minimized.

As regards the yields (about 66–69%) reported for the procedures described in the Examples 1–3, it is also apparent that if in a preparation the ethanol-containing mother liquors saturated with the desired product, coming from a previous preparation, were to be used, the yields would remarkably increase and approach 100%.

The present invention also relates to compositions which comprise the acetyl L-carnitine acid fumarate of the present invention as active ingredient and, optionally, a pharmacologically acceptable excipient.

The compositions can present themselves as pharmaceuticals, OTC compositions, nutritional supplements, dietary supplements, veterinary products or fodders.

The compositions according to the present invention can also comprise further nutritional or pharmacological active ingredients. In particular, the compositions can comprise other pharmacologically acceptable salts of L-carnitine and/or (C$_2$–C$_5$) alkanoyl L-carnitines.

The compositions can also comprise fillers, binders, lubricants, mold-release agents, flow-regulating agents, dispersing agents, colorants, flavoring agents and the like as it will be apparent to any expert in pharmaceutical technology or pharmacy.

The orally administrable, solid forms comprise tablets, chewable tablets, pills, troches, lozenges, capsules, powders or granulates.

In case of powders or granulates the presentation form can occur as sachets.

Compositions in unit dosage form shall comprise an amount of acetyl L-carnitine acid fumarate of the present invention corresponding to 50–500, preferably 100–250, milligrams of acetyl L-carnitine inner salt.

Optionally, further active ingredients, antioxidants and nutrients may supplement the compositions of the invention such as Vitamin C, Vitamin E, B Vitamins (B$_6$, B$_{12}$ and folic acid) Coenzyme Q$_{10}$ and α-lipoic acid.

As it will be apparent to any expert in pharmaceutical technology or pharmacy, the compositions for sachets may comprise suitable excipients such as fructose, citric acid, saccharin sodium, tonic water flavour, D-mannitol and colloidal silicon dioxide.

The composition for tablets and chewable tablets may comprise excipients such as mint essence, saccharin sodium, sorbitol solution, sorbitol, magnesium stearate, talc, pregelatinized corn starch, mannitol and saccharose.

Thanks to the stability and non-hygroscopicity of the substance of the present invention the compositions for capsules can be entirely free of excipients, in view of the chemical inertness of the ingredient towards the gelatinous material the capsules are made of.

What I claim is:

1. A solid, crystalline, non-hygroscopic substance having melting point of 105–110° C. which is acetyl L-carnitine acid fumarate.

2. A composition comprising:
   (i) a solid, crystalline, non-hygroscopic substance having melting point of 105–110° C. which is acetyl L-carnitine acid fumarate; and
   (ii) a pharmacologically acceptable excipient.

3. A process for preparing a solid, crystalline, non-hygroscopic substance having melting point of 105° C.–110° C. which is acetyl L-carnitine acid fumarate, which comprises the following steps:
   (a) preparing a crystallization seed consisting essentially of acetyl L-carnitine acid fumarate by
      (a.1) adding equimolar amounts of acetyl L-carnitine inner salt and fumaric acid to a lower alkanol, heating and stirring the resulting reaction mixture till complete dissolution of the reagents, thus obtaining a solution;

(a.2) cooling the solution to room temperature and adding thereto a precipitating agent in the minimum amount needed to obtain the formation of a precipitate of acetyl L-carnitine acid fumarate;

(a.3) filtering off and drying the precipitate to be used as crystallization seed in step (c);

(b) preparing a solution of equimolar amounts of acetyl L-carnitine inner salt and fumaric acid in a lower alkanol, heating and stirring the resulting reaction mixture till complete dissolution of the reagents and then cooling the solution to room temperature;

(c) seeding the solution of step (b) with the minimum amount of the crystallization seed of step (a) needed to obtain a precipitate;

(d) isolating the precipitate of step (c) by filtering it off and drying it in an oven under vacuum thus obtaining a solid, crystalline, non-hygroscopic substance comprised of acetyl L-carnitine acid fumarate, having melting point of 105° C.–110° C.

4. The process of claim 3, wherein the lower alkanol is selected from the group consisting of methanol, ethanol, propanol, isopropanol, butanol, isobutanol and the aqueous solutions thereof.

5. The process of claim 3 wherein the lower alkanol is absolute ethanol or 95%–96% v/v ethanol.

6. The process of claim 3, wherein the precipitating agent of step (a.2) is selected from the group consisting of L-carnitine acid fumarate, the chlorides, carbonates and sulphates of alkali metals and alkaline-earth metals, silica and alumina.

7. The process of claim 3, wherein the precipitating agent of step (a.2) is selected from the group consisting of chlorides, carbonates and sulphates of alkali metals and alkaline earth metals selected from the group consisting of sodium, potassium, magnesium and calcium.

8. The process of claim 3, wherein the minimum amount of the precipitating agent of step (a.2) and crystallization seed of step (c) is about 0.01–0.5% by weight to the amount of acetyl L-canitine inner salt and fumaric acid.

9. The process of claim 3, wherein in step (c) the seeded solution is cooled down to below room temperature.

10. A process for preparing a solid, crystalline, non-hygroscopic substance having melting point of 105° C.–110° C. which is acetyl L-carnitine acid fumarate, which comprises the following steps:

(i) preparing a solution of equimolar amounts of acetyl L-carnitine inner salt and fumaric acid in a lower alkanol, heating and stirring the resulting reaction mixture till complete dissolution of the reagents and then cooling the solution to room temperature;

(ii) seeding the solution of step (i) with the minimum amount of a crystallization seed consisting essentially of acetyl L-carnitine acid fumarate needed to obtain a precipitate; and (iii) isolating the precipitate of step (ii) by filtering it off and drying it in an oven under vacuum thus obtaining a solid, crystalline, non-hygroscopic substance comprised of acetyl L-carnitine acid fumarate, having melting point of 105° C.–110° C.

11. The process of claim 10, wherein the lower alkanol is selected from the group consisting of methanol, ethanol, propanol, isopropanol, butanol, isobutanol and the aqueous solutions thereof.

12. The process of claim 10, wherein the lower alkanol is absolute ethanol or 95%–96% v/v ethanol.

13. The process of claim 10, wherein in step (ii) the seeded solution is cooled down to below room temperature.

14. The process of claim 3, wherein in step (c) the seeded solution is cooled down to about 0° C.–10° C.

15. The process of claim 10, wherein in step (ii) the seeded solution is cooled down to about 0° C.–100° C.

* * * * *